United States Patent [19]

Cronan

[11] Patent Number: 4,646,562
[45] Date of Patent: Mar. 3, 1987

[54] METHOD AND APPARATUS FOR DETECTING RELATIVE DYNAMIC LIQUID SURFACE ACTIVITY

[75] Inventor: Charles L. Cronan, Shorewood, Wis.

[73] Assignee: Miller Brewing Company, Milwaukee, Wis.

[21] Appl. No.: 839,838

[22] Filed: Mar. 13, 1986

Related U.S. Application Data

[63] Continuation-in-part of Ser. No. 666,355, Oct. 30, 1984, abandoned.

[51] Int. Cl.$^4$ ............................................. G01N 13/02
[52] U.S. Cl. ....................................................... 73/64.4
[58] Field of Search ........................................ 73/64.4

[56] References Cited

U.S. PATENT DOCUMENTS

| | | | |
|---|---|---|---|
| 2,473,553 | 6/1949 | Stokes | 73/64.4 |
| 3,096,642 | 7/1963 | Peterson | 73/53 |
| 3,913,385 | 10/1975 | Jobe | 73/61.1 R |
| 4,228,677 | 10/1980 | Olsson | 73/64.4 |
| 4,361,032 | 11/1982 | Lessnig | 73/64.4 |
| 4,416,148 | 11/1983 | Klus et al. | 73/64.4 |

FOREIGN PATENT DOCUMENTS

| | | | |
|---|---|---|---|
| 26470 | 2/1980 | Japan | 73/64.4 |
| 972331 | 11/1982 | U.S.S.R. | 73/64.4 |

OTHER PUBLICATIONS

Pilz, et al., Automatic Monitor for Surfactants in Aviation Turbine Fuel, *Analytical Chemistry*, vol. 43, No. 4, Apr. 1971.
A Surfactant Bee Venom Fraction: Separation on a Newly Devised Constant-Flow-Rate Chromatographic Column and Detection by Changes in Effluent Drop Volume, W. H. Shipman et al., U.S. Naval Radiological Defense Laboratory, dated Jul. 21, 1968.
Automated Drop Volume Apparatus for Surface Tension Measurement, E. L. Rowe, *Journal of Pharmaceutical Science*, vol. 61, No. 5, pp. 781-782, (1972).
Drop Weight Variation in an Automated Collection Procedure and its Relationship to Apparent Surface Tension, T. Exner et al., *Bio-Chimica et Biophysica Acta*, vol. 428, pp. 772-778, (1976).
An Automated Drop Weight Method Using a Drop-Counter-Regulated Fraction Collector for Measuring Surface Tension, T. Exner et al., *Science Tools*, vol. 23, No. 1, pp. 1-3, (1976).
A Surface Tension Apparatus According to the Drop Volume Principle, *Journal of Colloid and Interface Science*, vol. 60, No. 1, Jun. 1, 1977.
Pulse Duration Receiver Sales Literature Published by Moore Industries Incorporated.

*Primary Examiner*—Stewart J. Levy
*Assistant Examiner*—Joseph W. Roskos
*Attorney, Agent, or Firm*—Quarles & Brady

[57] ABSTRACT

A method and apparatus for continuous monitoring of the relative dynamic surface activity of a liquid in which the surface activity can be rapidly changing is disclosed. The liquid is flowed through an orifice at a constant volume flow rate to produce liquid drops. The time intervals between successive drops from the orifice are measured. Variations in the time intervals of pairs of two successive drops provide an indication of the volume of the second drop of each pair and thus provide an indication of the relative dynamic surface activity of the second drop. The measured time intervals are converted into electrical signals which are representative of the respective measured time intervals. The method and apparatus can be applied to liquid chromatography separations to continuously and quickly provide information about surface active components of the liquid and is especially applicable when only a small volume of the sample liquid is available. The method and apparatus can also be applied to industrial process monitoring and to use as a general laboratory instrument or method.

6 Claims, 3 Drawing Figures

FIG. 2 GEL PERMEATION CHROMATOGRAPHY
OF WHOLE BEER
2A. 280 nm ABSORBANCE
2B. SURFACE ACTIVITY
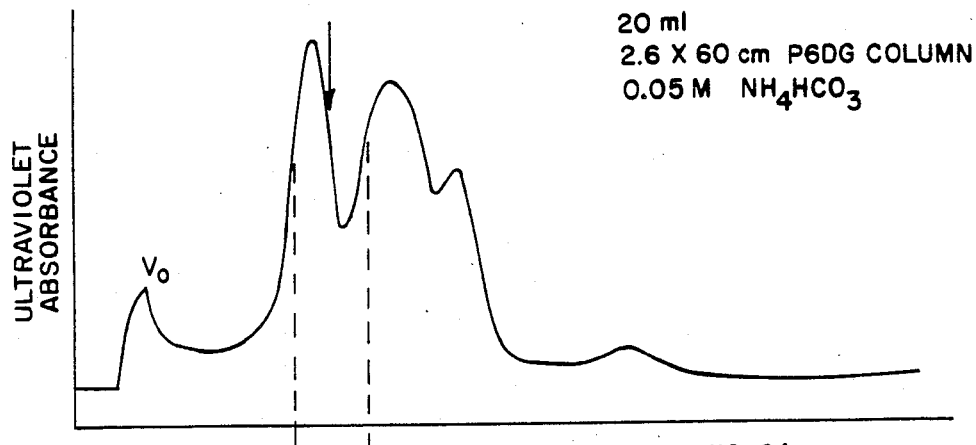
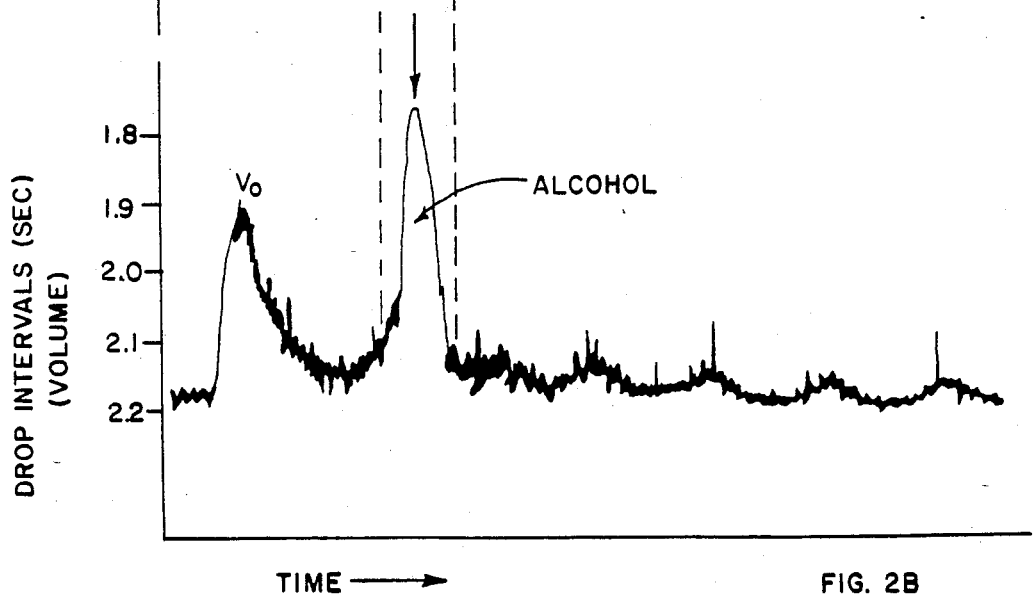

METHOD AND APPARATUS FOR DETECTING RELATIVE DYNAMIC LIQUID SURFACE ACTIVITY

This application is a continuation-in-part of application Ser. No. 666,355, filed Oct. 30, 1984, now abandoned.

FIELD OF THE INVENTION

The present invention relates to a method and apparatus for detecting the changing presence of surface active agents in a liquid. It relates to a method and apparatus particularly useful for the continuous on-line detection of changes in the surface tension of a liquid undergoing a chemical reaction or separation.

BACKGROUND OF THE INVENTION

Liquid surface activity is related to liquid surface tension. As surface activity increases, surface tension decreases. Therefore, measuring relative liquid surface tension enables the detection of liquid surface activity.

"Dynamic surface tension" refers to the apparent surface tension of a fluid surface in which the surface activity has not reached equilibrium. A drop which is formed infinitely slowly would give the equilibrium value of surface tension—this is the classical definition of surface tension. A drop which was growing only five seconds has a "dynamic" surface tension if its surface activity has not reached equilibrium. For some solutes which quickly equilibrate, such as ethanol, dynamic effects would not appear until drop intervals well under 0.1 seconds are achieved. However, some surface active proteins, such as those found in beer, can literally take hours to equilibrate. Practically speaking, it is excruciatingly difficult to measure their "equilibrium" surface tension, by any means. However, sufficient effects occur at such surfaces after only seconds so that dynamic surface tension can be measured to detect surface activity.

There are many techniques for the measurement of liquid surface tension. The DuNouy ring, Wilhelmy plate, capillary rise, maximum bubble pressure, and drop weight or drop volume methods are some of the most popular techniques. These techniques are generally employed on pure liquids and/or some solutions for equilibrium surface tension measurements. In addition, they can also be used to follow relatively slow dynamic or non-equilibrium changes in surface tension.

However, most of the prior art techniques are not amenable to total automation in order to monitor the surface tension, and therefore the surface activity, of a liquid having a continuously and relatively rapidly changing solute concentration. This need may arise, for example, in the monitoring of industrial effluents, chemical processing, reaction progress, or chromatographic eluate.

For example, in liquid chromatography, a mixture of substances are separated based upon the physical or chemical nature of the substances. A solution of the mixture is applied to the top of a chromatography column or injected into the eluent (a flushing liquid) which is pumped at constant volume flow over a usually solid or gel-like material called the chromatography packing.

The packing material is usually encased in a glass or stainless steel cylinder called the chromatography column. The packing material interaction with a particular component of the applied mixture determines the rate which the component travels the length of the column. For example, a packing material which operates by a "size-exclusion" mechanism has a generally porous structure; small molecules are trapped within these pores. The smaller molecules are thus slowed in their travel of the length of the column. Consequently, large molecules will exit in the column eluate (the liquid exiting the column) well before molecules which are smaller than the pore size of the packing.

Other separations are based upon chemical or physical attraction to the packing material such as in ion-exchange chromatography. Such packing material can completely prevent passage of particular classes of chemical structure allowing only non-binding compounds to pass unhindered. The bound substances can be released by means of a specially prepared eluent.

If an eluting component is surface-active, it will change the surface activity of the eluate from the chromatography column. Therefore, monitoring the surface activity of the eluate yields information on the presence or nonpresence of the component. Automatically providing this information, quickly, and in some applications with only a very small sample, has not been available in the prior art.

Only one of the surface tension techniques mentioned above, maximum bubble pressure, appears to have been adapted to a completely automated instrument as disclosed in the Klus et al. U.S. Pat. No. 4,416,148, issued Nov. 22, 1983. However, it cannot be employed for measuring small (less than 1 mL) liquid sample volumes. Therefore, it would be desirable to have a method and apparatus for measuring the relative liquid dynamic surface tension of small sample volumes in an automated and continuous manner.

SUMMARY OF THE INVENTION

The present invention provides a method of continuously monitoring the relative dynamic surface activity of a liquid and an apparatus for performing the method.

The method of continuously monitoring the dynamic surface activity of a liquid in which the surface activity can be rapidly changing includes flowing the liquid through an orifice at a constant volume flow rate to produce liquid drops. The time intervals between successive drops of liquid from the orifice are measured. Variations in the time intervals of pairs of two successive drops provide an indication of the volume of the second drop of each pair and thus provide an indication of the dynamic surface activity of the second drop. The measured time intervals are converted into electrical signals which are representative of the respective measured time intervals. In this way, a continuous indication of the relative dynamic surface activity of the liquid is provided. The method is especially applicable to small (less than 1 mL) volumes of sample liquid because surface activity information is provided with only two drops.

In an especially useful application of the invention, an apparatus is provided for detecting the dynamic surface activity of an eluate produced in a chromatographic separation of the constituents of a sample liquid. The apparatus includes a chromatography column and a packing material in the chromatography column for interacting with one or more constituents of the sample liquid to vary the rate the constituents flow through the column. This provides the eluate at the discharge of the column. Pump means flow the sample liquid through the packing material in the chromatography column at a constant volume flow rate. The eluate is directed at the constant volume flow rate to an orifice for forming a series of falling drops. Detector means sense each drop of the series of falling drops formed by the orifice and provide a signal to indicate the presence of each drop. Measuring means responsive to the detector means signal for measuring the time intervals between the drops of each of a series of pairs of two successive drops provides an output signal that varies in accordance with the time interval of each pair. Variation in the measuring means output signal provides an indication of the presence of surface active constituents in the second drop of each pair of two successive drops. This apparatus is especially applicable to various analytical assays in biomedical, biochemical, chemical and surfactant research in which only a small volume of sample liquid is available, or where the assay must be provided quickly or continuously.

The invention also finds unique application in monitoring the progress of a liquid body undergoing a chemical reaction in which the presence of surface active constituents is changing. By monitoring the relative dynamic surface activity in the manner provided by the method, the progress of the chemical reaction can be determined easily and quickly.

Other objects, advantages and potential uses of the invention will be apparent to those skilled in art from the description and the drawings.

BRIEF DESCRIPTION OF THE DRAWINGS

FIG. 2a is a plot of the absorbance versus time for a low pressure gel permeation liquid chromatographic separation of whole beer taken at 280 nm; and FIG. 2b is a plot of the output voltage of the surface tension detector of FIG. 1 for the whole beer sample subjected to the low pressure gel permeation liquid chromatographic separation for the conditions depicted in FIG. 2a, illustrating that only two surface active fractions elute.

DETAILED DESCRIPTION OF THE PREFERRED EMBODIMENTS

Figure 1:
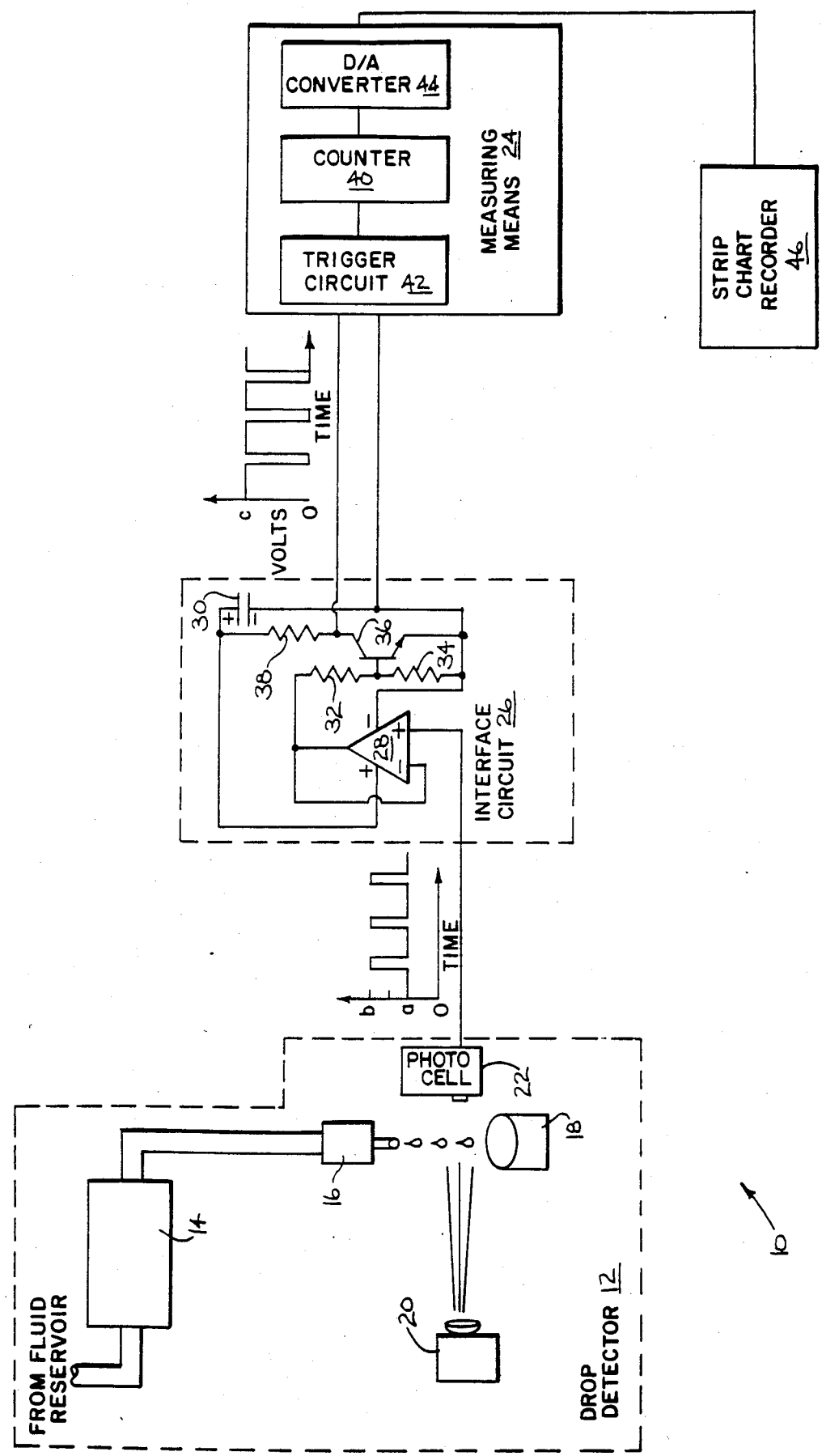
FIG. 1 is a block schematic diagram of an embodiment of the surface activity detector of the present invention.

FIG. 1 is a block diagram of a surface activity detector 10 of the present invention. The surface activity detector 10 includes a drop detector 12 for indicating the fall of drops of a liquid such as beer, the surface activity of which is to be monitored. In practice, the drop detector 12 typically includes a liquid feeder 14 such as a pump or a gravity feeder which supplies the liquid under study from a reservoir (not shown) to an orifice 16 where the liquid is made to drip into a drain container 18. The pressure of the liquid feeder 14 and the radius of the orifice 16 are selected in accordance with the density of the liquid to form drops at the orifice 16. When the flow rate of the liquid through the orifice is made constant, the product of the time interval between drops and the volume flow rate equals the drop volume. Thus, the time interval between drops is directly proportional to the drop volume. The volume of each drop is, in turn, nearly directly proportional to the liquid dynamic surface tension. Therefore, the time interval between drops is nearly directly proportional to the liquid's dynamic surface tension, which is representative of the surface activity of the liquid.

The proportionality factor of the time interval between drops to the dynamic surface tension depends upon the fluid flow rate, the fluid density, the fluid temperature, the geometry of the drop shape and the orifice size. Since density is not known exactly (the solute concentration can vary), especially for chromatographic eluate, the drop time intervals are referred to as "nearly" directly proportional to the dynamic surface tension. An exact value for the dynamic surface tension could be attained by holding the fluid temperature constant and flowing the fluid through a flow-through densitometer device (not shown) which would measure the fluid density. This could be input to a data processor, together with the time interval measurements (explained below) so that the exact dynamic surface tension could be computed since the equation relating surface tension to fluid density, drop volume and drop geometry or orifice size is well documented. These corrections would be desirable if the invention were to be applied to measuring dynamic surface tension. However, if the invention is only applied to monitoring relative surface activity, under most conditions they need not be applied.

To detect the passage of time between the complete formation of successive drops falling from the orifice 16 into the drain container 18, a highly collimated light beam from a light source 20 is directed at right angles to the path of liquid drop travel between the orifice 16 and the drain container 18. A photoelectric cell detector 22 such as a phototransistor, a photodiode, a photodector tube, a photoresistor or some other photodetecting means is positioned in registration with the light source 20 on the opposite side of the orifice 16 to receive the light beam from the light source 20. The light beam from the light source 20 is made sufficiently narrow so as to be interrupted or broken when a liquid drop crosses the light beam before dropping into the drain container 18.

The particular type of drop detector employed is not critical to the invention. Detection techniques other than photodetection are possible. Examples include mass detection, conductivity detection and acoustic detection. However, photodetection is easily implemented and is particularly non-invasive. A commercial device which is suitable and easily adapted for this purpose is the Model No. 120310 drop detector which is available from Gilson Medical Electronics, Middleton, Wis.

If a photoelectric cell detector is employed in the invention, its output signal will normally be a relatively low voltage (a in FIG. 1) for intervals when the light beam from the light source 20 impinges on the photoelectric cell detector 22. When the light beam is interrupted by the passage of a drop, the photoelectric cell detector output signal will suddenly rise to b volts and will remain at b volts until the drop passes through the light beam and the beam again becomes incident upon the photoelectric cell detector 22. The output signal of the photoelectric cell detector 22 when plotted as a function of time therefore appears as a train of narrow pulses having a peak amplitude of b volts and a quiescent amplitude during intervals between the pulses of a volts as shown in FIG. 1. The time interval between the pulses of the photoelectric cell output signal represents the time interval between drops. When the flow rate through the orifice is held constant, the time interval between the pulses of the photoelectric cell detector output signal is nearly directly proportional to the surface tension and therefore indicates the relative surface activity of the liquid.

By itself, the output signal of the photoelectric cell detector 22 does not provide a very useful indication of the dynamic surface tension of the fluid. While the photoelectric cell 22 output signal can be plotted and the time between peaks can be measured to provide an indication of dynamic surface tension, such a measurement does not provide a real-time, or running, indication of the dynamic surface tension of the fluid. In many laboratory experiments, a running indication of dynamic surface tension is very useful. In particular, it is often desirable to have a running indication of the dynamic surface tension of a liquid which is undergoing chromatographic separation in order to determine if there are any surface active fractions that have eluted for selective collection or rejection.

In order to obtain a running measurement of the dynamic surface tension thereby allowing the surface activity of a liquid to be studied as the liquid undergoes chromatographic separation, a measuring means 24 is provided. The measuring means 24 can be coupled to the photoelectric cell detector 22 by an interface circuit 26. The measuring means 24 measures the time interval between voltage amplitude shifts of the photoelectric cell detector 22 output signal as conditioned per the interface circuit 26 and generates an output signal which varies in accordance with the measured time interval. Since the time interval between voltage amplitude shifts of the photoelectric cell output voltage corresponds to the drop volume of the liquid leaving the fluid orifice 16, and since at constant flow rate the drop volume is nearly proportional to the dynamic surface tension, the output signal of the measuring means 24 is nearly proportional to the dynamic surface tension. Since a change in the dynamic surface tension indicates a change in surface activity, the measuring means output signal can be used to detect changes in surface activity.

The interface circuit 26 couples the drop detector 12 to the measuring means 24. The interface circuit 26 of FIG. 1 operates to shift the amplitude of the output voltage of the photoelectric cell detector 22 and invert its polarity to enable the measuring means 24 to better measure the time interval between peaks of the photoelectric cell detector output voltage. In practice, the interface circuit 26 includes an operational amplifier 28 with positive and negative (+) and (−) power inputs which are coupled to the positive and negative outputs of a voltage supply, represented by a battery 30. The operational amplifier 28 has its noninvert (+) input coupled to the output of the photoelectric cell detector 22. The invert (−) input of the operational amplifier 28 is coupled to the operational amplifier output which is coupled by a pair of serially-connected resistors 32 and 34 to the negative terminal of the battery 30. The junction between the resistors 32 and 34 is coupled to the base of an NPN transistor 36. A resistor 38 is coupled between the positive terminal of the battery 30 and the collector of the transistor 36 and the emitter of the transistor is coupled to the negative battery terminal.

The values of the resistors 32 and 34 are selected such that the transistor 36 is forward biased when the output voltage of the operational amplifier 28 rises in response to an increase in the output voltage of the photoelectric cell detector 22 above its quiescent value of a volts. When the transistor 36 is forward biased, the transistor 36 becomes conductive, causing the voltage at the junction between the resistor 38 and the transistor 36 collector (as measured with respect to the negative terminal of battery 30) to fall from a nominal value approximately equal to the voltage of the battery 30 (c volts) to approximately zero volts. The interface circuit 26 output signal appears between the junction of the resistor 38 and the transistor 36 collector and the negative terminal of the battery 30. When plotted against time, the interface circuit 26 output signal appears as a pulse signal which is inverted from the pulse output signal of the photoelectric cell detector 22. The amplitude of the interface circuit 26 output signal deviates from a quiescent value of approximately the voltage across the battery (c volts) to an amplitude of approximately zero volts each time the photoelectric cell detector 22 output signal rises from a quiescent amplitude of a volts to approximately b volts, as occurs each time a drop of liquid interrupts the beam of light impinging on the photoelectric cell detector 22.

The measuring means 24 of the embodiment of FIG. 1 is commercially known as a pulse duration receiver and is available from Moore Industries Incorporated, Sepulveda, California. It includes a counter 40 for counting through the time interval between amplitude deviations of the interface circuit 26 output signal. That is, it counts during the time interval when the output voltage of the interface circuit 26 is at c volts. The counter 40 ceases counting when a trigger circuit 42 senses a drop in the output voltage of the interface circuit 26. This also causes the counter contents to be transferred to a digital-to-analog converter 44 which converts the count into an analog voltage. The counter 40 resumes counting when the output signal of the interface circuit 26 returns to a magnitude of c volts. The analog voltage produced is proportional in magnitude to the count of the counter 40 and the digital-to-analog converter 44 maintains this signal until the counter 40 is reset by the trigger circuit 42. This occurs when the next drop falls from the orifice 16 and interrupts the light beam impinging on the photoelectric cell detector 22. Thereby, the counting cycle starts all over again. The output voltage of the digital-to-analog converter 44 of the pulse duration receiver 24 can be visually displayed, either on a strip chart recorder 46, an oscilloscope (not shown) or any other suitable output means to provide a visual indication of the dynamic surface tension and therefore of the surface activity of the liquid.

In the embodiment using the Gilson Medical Electronics Model No. 120310 drop detector and the Moore Industries, Inc. pulse duration receiver, the following particular parameters were found to perform adequately. It was found that the drop detector had a quiescent voltage "a" approximately equal to 2.5 volts. Its pulse voltage amplitude "b" was found to be about 5 volts. A battery 30 providing 9 volts across its terminals was chosen so that "c" was about 9 volts. Resistors 32 and 34 were chosen to provide a voltage divider to trigger the transistor 36, which would not turn on unless the voltage at its base was at least 0.7 volts.

The only purpose of the interface circuit 26 is to condition the output signal of the drop detector 12 to be suitable to be input to the measuring means 24. There are a number of ways of performing this function, the requirements of which will be determined by the particular type of drop detector and the particular type of measuring means which are chosen. Of course, there are also different ways of conditioning the output signal of a particular drop detector to be input to a particular measuring means. For example, a Schmitt trigger inverter could be used to perform the same conditioning function as the interface circuit 26 of FIG. 1 and may be preferable in some applications. Also, considering the wide range of possible alternatives for both the drop detector 12 and the measuring means 24, the output of the drop detector 12 could be matched to the input of the measuring means 24. This would obviate the need for any interface circuit and the drop detector 12 could be coupled directly to the measuring means 24. One example of this is that, if the output voltage of the drop detector 12 was low enough during the interval between drops (voltage a), a microprocessor could be used as the measuring means and could be connected directly to the drop detector output.

In some applications, it may be preferable to use a data processor such as a general purpose computer or a microprocessor as the measuring means. For example, if a microprocessor is used, its input port could possibly be connected to the output of the drop detector 12 if the microprocessor and the drop detector were compatible as pointed out above. If not, it may be necessary to use some interface means, such as a Schmitt trigger inverter or an analog to digital converter, to condition the drop detector output signal to be suitable to be input to the data processor.

Using a microprocessor or computer as the measuring means would enable a number of ways of measuring the time interval between drops. One way would be by continuous monitoring. In continuous monitoring, the input port is read and if no drop is detected, a register or memory byte is incremented. This repeats until a drop is detected at which time the total count, representing the time interval since the previous drop, can be scaled to time and output. The count accumulators are then cleared and the microprocessor begins again to monitor the input port for a drop signal.

Another way to measure the time interval between drops would be to control the count of the microprocessor by interrupt signals. The microprocessor would be in a counting loop. The signal produced by a falling drop would generate an interrupt signal which causes the microprocessor to jump to the portion of the program which outputs the count. When that portion of the program is completed, the microprocessor returns to its counting loop.

Yet another way to determine the time interval between successive drops would be to directly measure it with a built-in clock which is provided in some data processors. The built-in clock could be used to automatically measure the time interval between drops and the measured interval could be output.

An advantage of using a microprocessor or computer is that it can be programmed to measure a truer indication of the time interval between drops than the period the pulse duration receiver measures. As explained above, the pulse duration receiver begins counting when it senses a voltage rise from the interface circuit 26. This corresponds to the instant in time when a drop has passed through the collimated beam from the light source 20 and the beam has again become incident upon the photocell 22. The pulse duration receiver stops counting when it senses a decrease in the output voltage of the interface circuit 26 which corresponds to the time when a drop first interrupts the beam of the light source 20. There is a relatively short period of time between the time that the drop first interrupts the light beam and the time the drop has just passed through the beam so that the beam again becomes incident upon the photocell 22. This short period of time results in an error in the drop interval measured by the pulse duration receiver which is too short by the length of time which the light beam is interrupted by the falling drop. While this error is only about 10 msec and is considered negligible for purposes of detecting relative surface tension, there may be some applications where a very accurate measurement of the time interval is preferred.

A very accurate measurement of the time interval between drops can be provided by using a microprocessor or computer to measure the interval. The microprocessor or computer can be programmed to begin counting when it first senses an interruption in its input signal corresponding to when a drop first interrupts the light beam and to cease counting when it senses the next such interruption, which corresponds in time to the next drop first interrupting the light beam. This arrangement thereby eliminates the error attributable to the length of time the light beam is interrupted by a drop.

It may also be preferable to use a microprocessor or computer as the measuring means 24 if the measured time interval between successive drops is to undergo further processing. For example, a continuously moving or running average of the time interval between drops may be desirable. To this end, the microprocessor or computer can be programmed to compute the desired values. Typically, the moving average is calculated by (a) first obtaining n successive time intervals, (b) summing them and dividing by n which gives the average, (c) dropping the oldest of the n time intervals, (d) obtaining the next time interval, and (e) repeating steps (b) through (e) using only the last n values. Successive time averages can also be performed by collecting n successive values, averaging them and outputting the average value until the next n successive values are collected and averaged. The standard deviation or other statistical values could also be calculated and the resulting data could be scaled to time and output on a cathode ray tube, a printer, a strip chart recorder or any other suitable output means.

Program steps to perform further processing of the measured time interval by a microprocessor or computer could be incorporated into the portion of the program which outputs the data. Instead of outputting each count, the count would be stored to be used in the subsequent calculations. The time required for the calculations would probably be insignificant compared to the time between drops in most applications. However, if it was significant, the calculation time could be added as a constant to the initialization of the counting register or otherwise so that it would be included in the time interval before being output or further processed.

There are many alternative ways of practicing the invention in addition to those above. Other digital and/or analog circuitry could be used as, or in connection with, the measuring means in addition to the alternatives mentioned above. For example, the time interval could be converted to an analog voltage by use of capacitive charging or integration which could also be manipulated into a moving average value or other values.

The surface activity detector has many potential applications as a liquid chromatography detector. These include various analytical assays in biomedical, biochemical, chemical and surfactant research. An example of the results obtained from using the surface activity detector 10 of FIG. 1 as a liquid chromatography detector can be seen by referring to FIG. 2B. FIG. 2B is a plot of the pulse duration receiver 24 output voltage versus time. This was obtained from the separation of beer proteins by low pressure gel column chromatographic separation over an approximately 12 hour period. Specifically, a sample volume of whole beer (20 mL) was applied directly to the top of a 2.6 cm diameter chromatography column with a column length of 60 cm. The column was filled with a size-exclusion packing material, Bio-Gel P6DG (BioRad Laboratories, Richmond, CA). This packing material retards the flow of chemical species having molecular weights of less than approximately 6000 Daltons.

After the sample was applied to the top of the column, a cap was placed over the top of the column and any eluent was pumped through the column. The eluent employed was isocratic (i.e., of constant composition), 0.05 M ammonium bicarbonate. This eluent was pumped at constant flow rate to the top of the column, in a closed system with the entire eluate flow directed to the orifice. The pumping rate was adjusted to provide approximately one drop per second. The pump employed in this experiment was a Rainin Rabbit (Rainin Instruments, Woburn, MA) peristaltic pump.

The plot of ultraviolet absorbance versus time of the whole beer sample is provided in FIG. 2A for reference purposes. As will be appreciated from the comparison of FIGS. 2A and 2B, the $V_o$ (column void volume) surface active peak in FIG. 2B corresponds to the $V_o$ absorbance peak in FIG. 2A. The second surface active peak in FIG. 2B does not correspond to an absorbance peak in FIG. 2A but is due solely to the elution of alcohol.

In another application, a sample volume of only 0.1 mL was used in HPLC (high pressure liquid chromatography) size-exclusion separations of specific surface-active fractions of beer. The smaller sample volumes are made possible without loss of resolution by a narrow column diameter. In HPLC, the samples are usually injected into the eluent stream in between the pump discharge and the column inlet and the eluent is pumped at constant volume and at high pressure. Since the eluate flows at constant volume, it is compatible with and can be directed to the orifice of the surface activity detector 10.

One particularly life-saving liquid chromatography application could be the facilitation of a rapid assay for fetal lung surfactant in amniotic fluid. This information is of great importance for the obstetrician faced with early delivery of a fetus in a stressful condition or if the mother's life is endangered by delay. The pulmonary surfactant assay permits an estimation of the development of the fetus' lungs in order to predict the likelihood of respiratory complications. Current rapid assays are crude empirical methods of low reliability; more accurate methods require one or more days.

It is known that the chemical species of importance in amniotic fluid for the prediction of fetal lung development are lecithin and sphingomyelin. In particular, the ratio of these chemicals, termed the L/S ratio, is required. Since both of these species are surface-active, less than 1 mL of the amniotic fluid could be extracted and analyzed using the surface activity detector 10 as a liquid chromatography detector to provide this information accurately and in only a few minutes.

It is also known that blood plasma contains many surface active components. The plasma surfactant concentration profiles vary considerably from the norm for some specific diseases, especially those involving the liver. Again the surface activity detector could be used as a liquid chromatography detector to examine small volumes of blood plasma (small being defined as meaning less than 1 mL) to obtain a complete, accurate, and fast profile of surface-active components in blood.

As another example, the effluent or runoff from various industrial sewage lines can be examined for specific surface-active species (virtually all organic compounds) using appropriate chromatography conditions. A small sample would be applied to a chromatography column with the resulting output from the surface activity detector revealing the presence of specific pollutants. Such analyses could be done rapidly in-house for self-monitoring with the surface activity detector 10.

The surface activity detector 10 could also be applied to monitor industrial processes. For example, emulsion polymerizations such as those used in paint manufacture and other latex uses require the presence of surfactants in order to encourage the formation of polymer droplets. These emulsifiers (the surfactants) change in concentration as the droplets grow. The progress of this reaction can be monitored by pumping a small quantity of reaction mixture directly from the liquid body undergoing the chemical reaction (the vat of paint, etc.) through the surface activity detector at constant volume flow rate. The change in drop interval will indicate the progress of the reaction. The fast response of the surface activity detector 10 is especially useful for conditions of rapid change when quick decisions, such as whether to add a quenching agent to halt droplet growth, are required.

In addition, brewing, pharmaceutical, bioengineering, and gasohol production all require means to monitor the progress of a fermentation. Nearly all fermentations produce surface-active agents as final product or by-product. It is possible to divert liquid from the fermenter through the surface activity detector to monitor the progress of the reaction. Continuous flow is not required in these applications (although the flow still must be at the same constant rate each time the process is monitored) since fermentations progress at a slow rate; the surface activity detector needs only two drops to determine the levels of surface-active component. Therefore, the detector need only be used at infrequent intervals with minimal loss of reactants.

The surface activity detector 10 may also be used as a general purpose drop volume surface tension instrument. If a pump is used at a calibrated constant volume flow rate, the detector can be employed as a surface tension instrument. Only two drops are required to determine the drop volume (as the drop interval) which makes this application useful for extremely small samples. In addition, dynamic surface tension studies (the effect of liquid surface age upon surface tension) are now possible since the flow rate can be adjusted to provide rapid drop formation offering surface tension information for liquid surfaces of about 5 msec or more in age.

While only certain features of the invention have been shown by way of illustration, many modifications and changes will occur to those skilled in the art. Therefore, the invention should not be limited by the foregoing description, but only by the claims which follow.

I claim:

1. A method of continuously monitoring the dynamic surface activity of a sample liquid in which the surface activity can be rapidly changing, the steps of which comprise:
(a) flowing the liquid through an orifice at a constant volume flow rate to produce liquid drops;
(b) measuring the time intervals between successive drops of liquid from the orifice so that variations in the time intervals of pairs of two successive drops will provide an indication of the volume of the second drop of each said pair of two successive drops and thus the dynamic surface activity of said second drop; and
(c) converting the measured time intervals into electrical signals which are representative of the respective measured time intervals to provide a continuous indication of the dynamic surface activity of each drop relative to the other drops.

2. The method of claim 1, further comprising the steps of:
(a) calculating the average of a fixed number of successively obtained time interval values, each representing the dynamic surface activity of the liquid at a given time, by averaging the latest obtained said fixed number of successively obtained time interval values to obtain a moving average of the dynamic surface activity of the liquid; and
(b) continuously displaying the value of the moving average of the surface activity of the liquid.

3. An apparatus for detecting the dynamic surface activity of an eluate provided in a chromatographic separation of the constituents of a sample liquid, comprising:
a chromatography column;
a packing material in the chromatography column for interacting with one or more constituents of the sample liquid to vary the rate the constituents flow through the length of the column to provide the eluate at the discharge of the column;
pump means for flowing the sample liquid through the packing material in the chromatography column at a constant volume flow rate;
an orifice for forming a series of falling drops;
means for directing the eluate at said constant volume flow rate to the orifice;
detector means for sensing each drop of said series of falling drops formed by the orifice, said detector means providing a signal to indicate the presence of each said drop; and
measuring means responsive to the detector means signal for measuring the time interval between the drops of each of a series of pairs of two successive drops, said measuring means providing an output signal that varies in accordance with the time intervals of said pairs;
wherein variation in the measuring means output signal provides an indication of the presence of surface active constituents in the second drop of each pair of two successive drops; and
display means to provide a continuous indication of the dynamic surface activity of each drop relative to the other drops.

4. A method of monitoring the progress of a liquid body undergoing a chemical reaction in which the presence of surface active constituents is changing, comprising:
pumping a sample volume of the liquid at a constant volume flow rate through an orifice to form a series of falling drops of the sample;
detecting each drop of said series of falling drops;
measuring the time intervals between successive falling drops of the sample so that variations in the time intervals of pairs of two successive drops will provide an indication of variation in the dynamic surface activity of the second drop of each pair; and
converting the measured time intervals into electrical signals which are representative of the respective measured time intervals to provide an indication of the progress of the chemical reaction in each drop to continuously monitor the chemical reaction of the liquid body.

5. A method as in claim 4, wherein the sample volume is pumped directly from the liquid body undergoing the reaction to the orifice.

6. A method of analyzing the contituent components of a body of liquid, comprising:
taking a sample volume of less than one milliliter from the body of liquid;
flowing the sample volume together with an eluent liquid at a constant volume flow rate through a chromatography column to produce an eluate liquid discharge from the column;
flowing the eluate liquid at the constant volume flow rate through an orifice to form a series of drops;
measuring the time intervals between successive drops from the orifice so that variation in the time intervals of pairs of two successive drops will provide an indication of the dynamic surface activity of the second drop of each pair of said two successive drops; and
converting the measured time intervals into electrical signals which are representative of the respective measured time intervals to provide an indication of the dynamic surface activity of each drop relative to the other drops to thereby provide a continuous indication of the dynamic surface activity of the body of liquid.

* * * * *